(12) United States Patent
Ishiwata (10) Patent No.: US 10,588,719 B2
(45) Date of Patent: Mar. 17, 2020

(54) FIXTURE AND IMPLANT

(71) Applicant: NANTOH. CO., LTD, Numazu-shi, Shizuoka (JP)

(72) Inventor: Teruo Ishiwata, Numazu (JP)

(73) Assignee: NANTOH. CO., LTD, Numazu-shi (JP)

(*) Notice: Subject to any disclaimer, the term of this patent is extended or adjusted under 35 U.S.C. 154(b) by 0 days.

(21) Appl. No.: 16/090,686

(22) PCT Filed: Apr. 10, 2017

(86) PCT No.: PCT/JP2017/014603
§ 371 (c)(1),
(2) Date: Oct. 2, 2018

(87) PCT Pub. No.: WO2017/179517
PCT Pub. Date: Oct. 19, 2017

(65) Prior Publication Data
US 2019/0117342 A1    Apr. 25, 2019

(30) Foreign Application Priority Data

Apr. 12, 2016  (JP) .................................. 2016-079232
Apr. 12, 2016  (JP) .................................. 2016-079233
Apr. 12, 2016  (JP) .................................. 2016-079234

(51) Int. Cl.
*A61C 8/00*       (2006.01)
*A61C 13/225*     (2006.01)
(Continued)

(52) U.S. Cl.
CPC .............. *A61C 8/0012* (2013.01); *A61C 8/00* (2013.01); *A61C 8/008* (2013.01); *A61C 8/0016* (2013.01);
(Continued)

(58) Field of Classification Search
CPC ... A61C 8/0012; A61C 8/0016; A61C 8/0018; A61C 8/008; A61C 8/00; A61C 8/0065;
(Continued)

(56) References Cited

U.S. PATENT DOCUMENTS 5,681,167 A    10/1997  Lazarof
6,213,775 B1    4/2001  Reipur
(Continued)

FOREIGN PATENT DOCUMENTS

JP    11-501856 A    2/1999
JP    2001-507607 A    6/2001
(Continued)

OTHER PUBLICATIONS

International Search Report dated Jun. 13, 2017, issued in counterpart application No. PCT/JP2017/014603 (2 pages).
(Continued)

*Primary Examiner* — Heidi M Eide
(74) *Attorney, Agent, or Firm* — Westerman, Hattori, Daniels & Adrian (57) ABSTRACT

A fixture (10) to be embedded in a bone (H), comprising: a fixture body (11) through which a central hole (13) penetrates over the entire length thereof; and a cap body (21) which closes an opening on a root end side of the central hole (13). The cap body (21) has a first shaft section (24) to be fitted into the central hole (13). The central hole (13) has a first tapered hole section (14) which decreases in diameter from the root end side toward a top end side, and the cap body (21) has a first tapered shaft section (25) to be fitted into the first tapered hole section (14).

14 Claims, 7 Drawing Sheets

(51) Int. Cl.
*A61K 6/02* (2006.01)
*A61K 6/087* (2006.01)
(52) U.S. Cl.
CPC .......... *A61C 8/0018* (2013.01); *A61C 13/225* (2013.01); *A61K 6/0205* (2013.01); *A61K 6/087* (2013.01)
(58) Field of Classification Search
CPC .. A61C 8/0033; A61C 8/0068; A61K 6/0205; A61K 6/087
See application file for complete search history.

(56) References Cited

U.S. PATENT DOCUMENTS

| | | | | |
|---|---|---|---|---|
| 6,902,583 | B2* | 6/2005 | Gerbec | A61F 2/30734 623/23.47 |
| 2003/0125189 | A1* | 7/2003 | Castro | C04B 33/14 501/127 |
| 2007/0148621 | A1* | 6/2007 | Yakir | A61C 8/001 433/173 |
| 2009/0123890 | A1 | 5/2009 | Purga et al. | |
| 2009/0248089 | A1* | 10/2009 | Jacofsky | A61B 17/686 606/311 |
| 2010/0003638 | A1* | 1/2010 | Collins | A61C 8/0012 433/174 |
| 2011/0269103 | A1* | 11/2011 | Shimko | A61C 8/0033 433/173 |
| 2012/0077150 | A1 | 3/2012 | Goodman et al. | |
| 2016/0015483 | A1 | 1/2016 | Kumar et al. | |
| 2017/0014210 | A1* | 1/2017 | Rogers | A61C 8/0012 |

FOREIGN PATENT DOCUMENTS

| | | |
|---|---|---|
| JP | 2003-525690 A | 9/2003 |
| JP | 2004-113718 A | 4/2004 |
| JP | 2008-541901 A | 11/2008 |
| WO | 97/024996 A2 | 7/1997 |
| WO | 98/30170 A1 | 7/1998 |
| WO | 01/66033 A1 | 9/2001 |
| WO | 2006/128620 A2 | 12/2006 |
| WO | 2008/022635 A2 | 2/2008 |

OTHER PUBLICATIONS

Decision to Grant a Patent dated May 25, 2018, issued in counterpart Japanese Patent Application No. 2017-549531, w/English translation (6 pages).

Notification of Reasons for Refusal dated Jan. 9, 2018, issued in counterpart Japanese Patent Application No. 2017-549531, w/English translation (9 pages).

* cited by examiner

FIXTURE AND IMPLANT

TECHNICAL FIELD

The present invention relates to a fixture and an implant, e.g., a dental implant which is embedded in a jaw bone.

The present application claims priority on the basis of Japanese Patent Application Laid-Open No. 2016-079232, Japanese Patent Application Laid-Open No. 2016-079233, and Japanese Patent Application Laid-Open No. 2016-079234 filed on Apr. 12, 2016 in Japan, and the contents of the application are incorporated herein.

BACKGROUND ART

Implants to be embedded in bodies have been attracting attention. For example, when a tooth root of a permanent tooth is lost due to caries or breakage, a dental implant is inserted in a hole provided in an alveolar bone and fixed thereto.

This dental implant is composed of a fixture (artificial tooth root) to be fixed to an alveolar bone, and an abutment (supporting stage) connected to the fixture. An implant crown (artificial crown) is mounted on the abutment.

A dental implant (fixture, abutment) is formed of not only metals such as titanium and titanium alloys but also ceramics such as alumina and zirconia.

As described in Patent Document 1, a fixture has a central hole opening at its top end face. In the central hole, a tapered hole section is formed. A tapered shaft section is formed on the abutment, and inserted into the central hole and fitted into the tapered hole section.

The abutment is inserted into the central hole of the fixture, so that the tapered shaft section enters into the tapered hole section in a wedge-like manner. Thereby, the fixture and the abutment are connected to each other. The tapered hole section and the tapered shaft section are in close contact with each other, and repeatedly receive a fitting pressure.

PRIOR ART DOCUMENTS

Patent Documents

Patent Document 1: Japanese Patent Application Laid-Open No. 2004-113718

SUMMARY OF INVENTION

Problem to be Solved

The implant needs to be miniaturized for reducing a burden on a patient (wearer). For example, if an implant for upper front teeth is not sufficiently miniaturized, the fixture will reach a maxillary sinus (paranasal sinus) because a maxilla (alveolar process) is considerably thin.

However, if the implant is miniaturized, there is a problem that defects such as cracks are likely to occur in the central hole of the fixture. Thereby, the connection between the fixture and the abutment is insufficient, or the fixture is broken. In particular, since a ceramic is a brittle material, it does not plastically deform like a metal, cracks occur in the central hole, and the fixture is broken.

Since ceramics such as zirconia are polycrystalline, each crystal is oriented in a flow direction by powder injection molding. For this reason, a compact such as a fixture has anisotropy of the mechanical strength. The mechanical strength in the flow direction of the powder in a mold is increased, and the mechanical strength in the direction perpendicular thereto is decreased. In particular, when the implant is miniaturized, the anisotropy of the mechanical strength becomes obvious, and mechanical strength poverty of the fixture or the like becomes problematic.

In addition, the fixture and the abutment are often fastened to each other with a screw. The abutment is screwed into the fixture to connect them.

However, a ceramic implant seldom elastically deforms, and thus a high fastening force cannot be obtained. Thereby, there is a problem that the connection between the fixture and the abutment becomes unstable.

Furthermore, the dental implant has a problem that a sound (occlusal sound) different from that of the natural teeth is generated during occlusion. The occlusal sound of the dental implant annoys not only the patient himself but also his surrounding people.

However, no countermeasure against the unpleasant occlusal sound generated by the dental implant has been taken.

An object of the present invention is to provide a fixture and an implant which can be miniaturized and highly strengthened.

Also, an object of the present invention is to provide an implant capable of maintaining firmly-connected between a fixture and an abutment.

Furthermore, an object of the present invention is to provide an implant capable of reducing unpleasant occlusal sounds.

Solution to Problem

The first embodiment of the fixture according to the present invention is a fixture to be embedded in a bone, characterized in that it comprises a fixture body through which a central hole penetrates over the entire length of the fixture body, and a cap body which closes an opening on a root end side of the central hole.

The second embodiment of the fixture according to the present invention is characterized in that the cap body has a first shaft section to be fitted into the central hole, in the first embodiment.

The third embodiment of the fixture according to the present invention is characterized in that the central hole has a first tapered hole section which decreases in diameter from the root end side toward a top end side, and the first shaft section has a first tapered shaft section which decreases in diameter from the root end side toward the top end side, in the second embodiment.

The fourth embodiment of the fixture according to the present invention is characterized in that the first tapered hole section and the first tapered shaft section are formed so as to have a taper angle of 0.1° to 10°, in the third embodiment.

The fifth embodiment of the fixture according to the present invention is characterized in that the first tapered hole section and the first tapered shaft section have a length of 20% or more to 50% or less of the entire length of the fixture body, in the third or fourth embodiment.

The sixth embodiment of the fixture according to the present invention is characterized in that the fixture body comprises a locked section formed on an inner surface of the central hole, the cap body comprises a locking section formed on the first shaft section, and the locked section comes into contact with the locking section to restrain rotation of the cap body with respect to the fixture body, in any one of the second to fifth embodiments.

The seventh embodiment of the fixture according to the present invention is characterized in that the fixture body and the cap body are respectively formed by injection molding of a ceramic powder, in any one of the first to sixth embodiments.

The first embodiment of the implant according to the present invention is characterized in that it comprises a fixture according to any one of the first to seventh embodiments and an abutment having a second shaft section to be fitted into a central hole of the fixture.

The second embodiment of the implant according to the present invention is characterized in that the central hole has a second tapered hole section which decreases in diameter from a top end side toward a root end side, and the second shaft section has a second tapered shaft section which decreases in diameter from the top end side toward the root end side, in the first embodiment.

The third embodiment of the implant according to the present invention is characterized in that the second tapered hole section and the second tapered shaft section have a taper angle of 0.1° to 10°, in the second embodiment.

The fourth embodiment of the implant according to the present invention is characterized in that the second tapered hole section and the second tapered shaft section have a length of 40% or more to 70% or less of the entire length of the fixture body, in the second or third embodiment.

The fifth embodiment of the implant according to the present invention is characterized in that the root end face of the second shaft section is close to a bottom face of the central hole, in any one of the first to fourth embodiments.

The sixth embodiment of the implant according to the present invention is characterized in that the abutment is formed by injection molding of a ceramic powder, in any one of the first to fifth embodiments.

The seventh embodiment of the implant according to the present invention is characterized in that it comprises an elastic member which is disposed between the cap body and the abutment and connected to the cap body and the abutment, in any one of the first to sixth embodiments.

The eighth embodiment of the implant according to the present invention is characterized in that the elastic member is a joint screw having male screws formed on its both ends and screwed into female screws respectively formed on the cap body and the abutment, in the seventh embodiment.

The ninth embodiment of the implant according to the present invention is characterized in that the female screws are respectively formed on the top end face of the cap body and the root end face of the abutment, in the eighth embodiment.

The tenth embodiment of the implant according to the present invention is characterized in that the elastic member is made of a thermoplastic resin, in the eighth or ninth embodiment.

The eleventh embodiment of the implant according to the present invention is characterized in that the elastic member is made of a polyetheretherketone resin, in the tenth embodiment.

The twelfth embodiment of the implant according to the present invention is characterized in that it is a dental implant to be embedded in an alveolar bone, in any one of the first to eleventh embodiments.

Effects of Invention

According to the present invention, a fixture on which defects are rarely caused in the central hole can be achieved.

On the ceramic fixture, defects in the central hole can be prevented. Thus, it can be ensured to miniaturize the fixture and the implant.

Also, according to the present invention, it can be ensured that the fixture and the implant are highly strengthened because they are made as an integrated body (assembly) consisting of a plurality of members. The ceramic fixture and implant can be highly strengthened by lowering the anisotropy of the mechanical strength (dispersing the directionality).

DESCRIPTION OF EMBODIMENTS

Embodiments of the present invention will be explained with reference to the drawings. Various sizes and the like shown in the following description are merely examples.

Dental Implant 1

Figure 1:
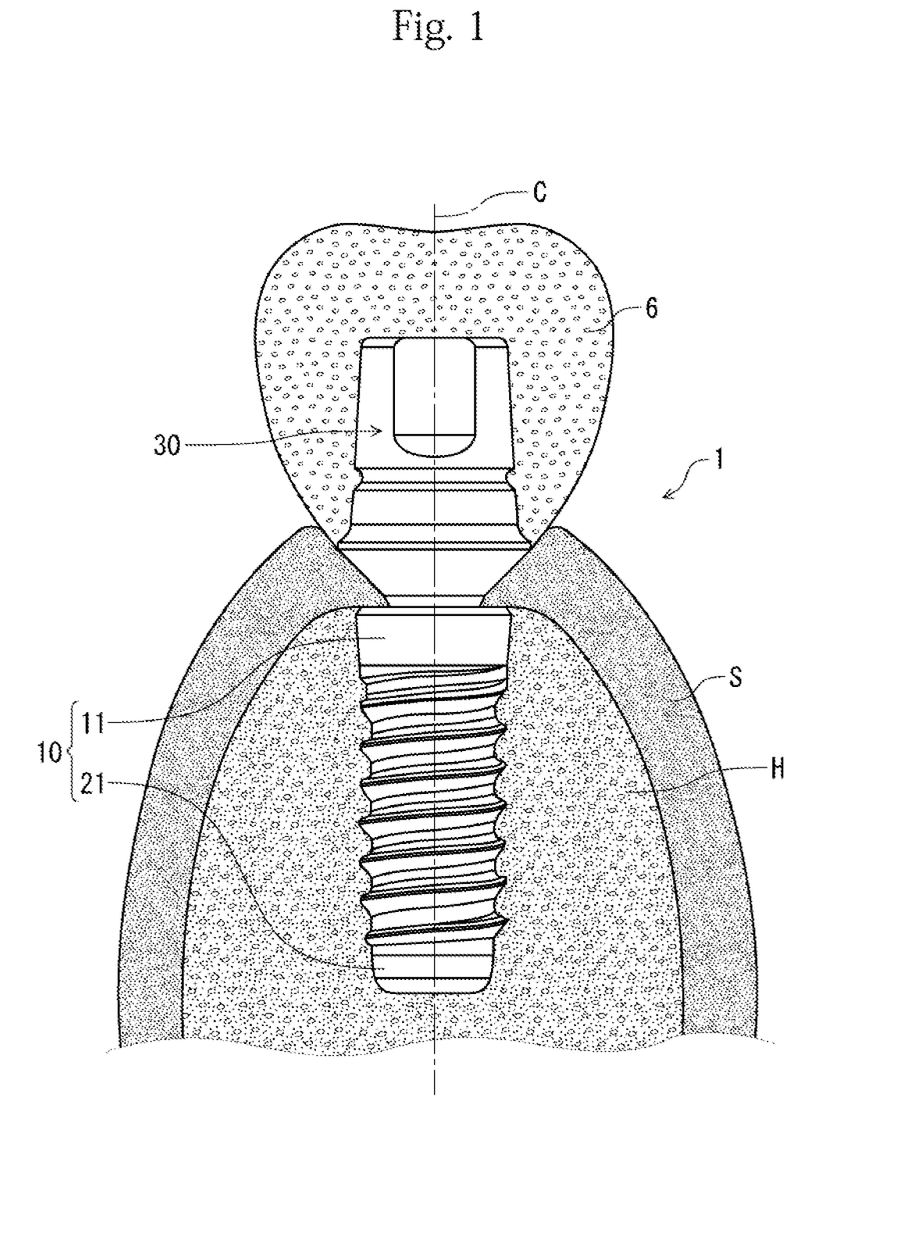
FIG. 1 illustrates a dental implant 1 according to an embodiment of the present invention.

FIG. 1 illustrates a dental implant 1 according to an embodiment of the present invention.

Figure 2:
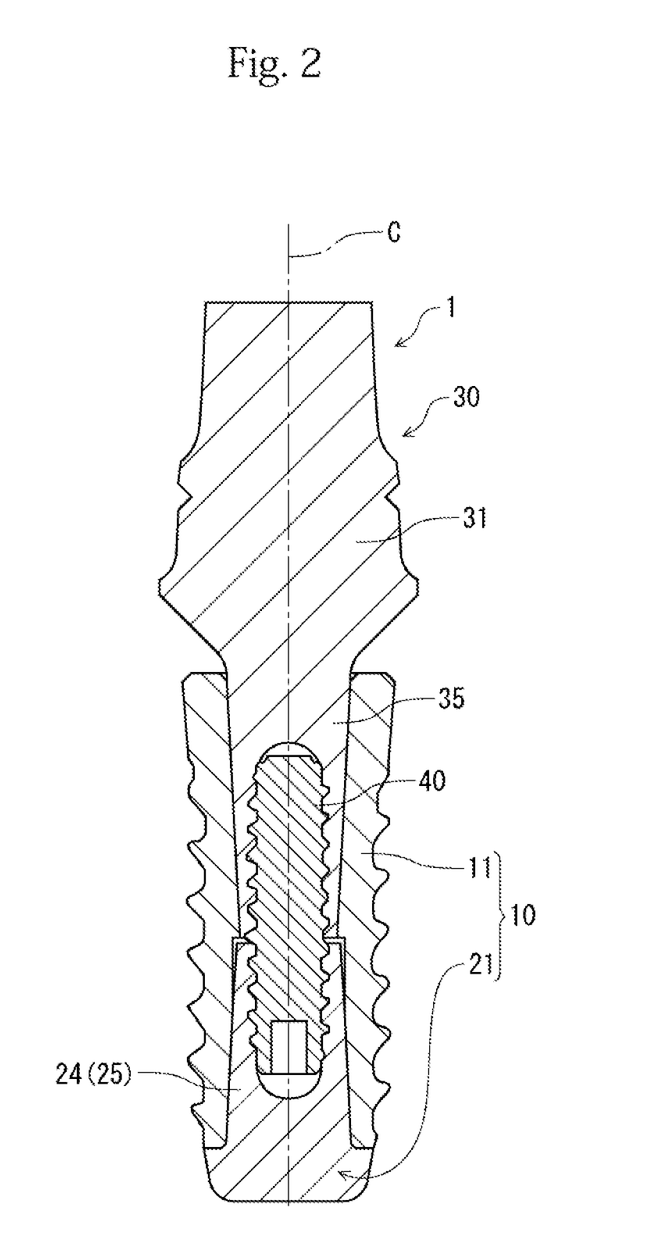
FIG. 2 illustrates a longitudinal sectional view of the dental implant 1.

FIG. 2 illustrates a longitudinal sectional view of the dental implant 1.

The dental implant (implant) 1 comprises a fixture 10 fixed to an alveolar bone (bone) H, and an abutment 30 fitted into the fixture 10. An implant crown 6 is mounted on the abutment 30.

A root end side below the implant crown 6 is covered with a gum S.

The longitudinal direction (direction along a central axis C) of the dental implant 1 is referred to as a Z direction or a vertical.

In the Z direction, the side of the implant crown 6 is referred to as a −Z direction or a top end side. The end in the −Z direction is referred to as a top end (first end). In the Z direction, the side of the fixture 10 is referred to as a +Z direction or a root end side. The end in the +Z direction is referred to as a root end (second end). A figure viewed from the −Z direction is referred to as a top view, and a figure viewed from the +Z direction is referred to as a bottom view.

The direction orthogonal to the Z direction is referred to as a radial direction. The direction around the central axis C is referred to as a circumferential direction.

Fixture 10

Figure 3:
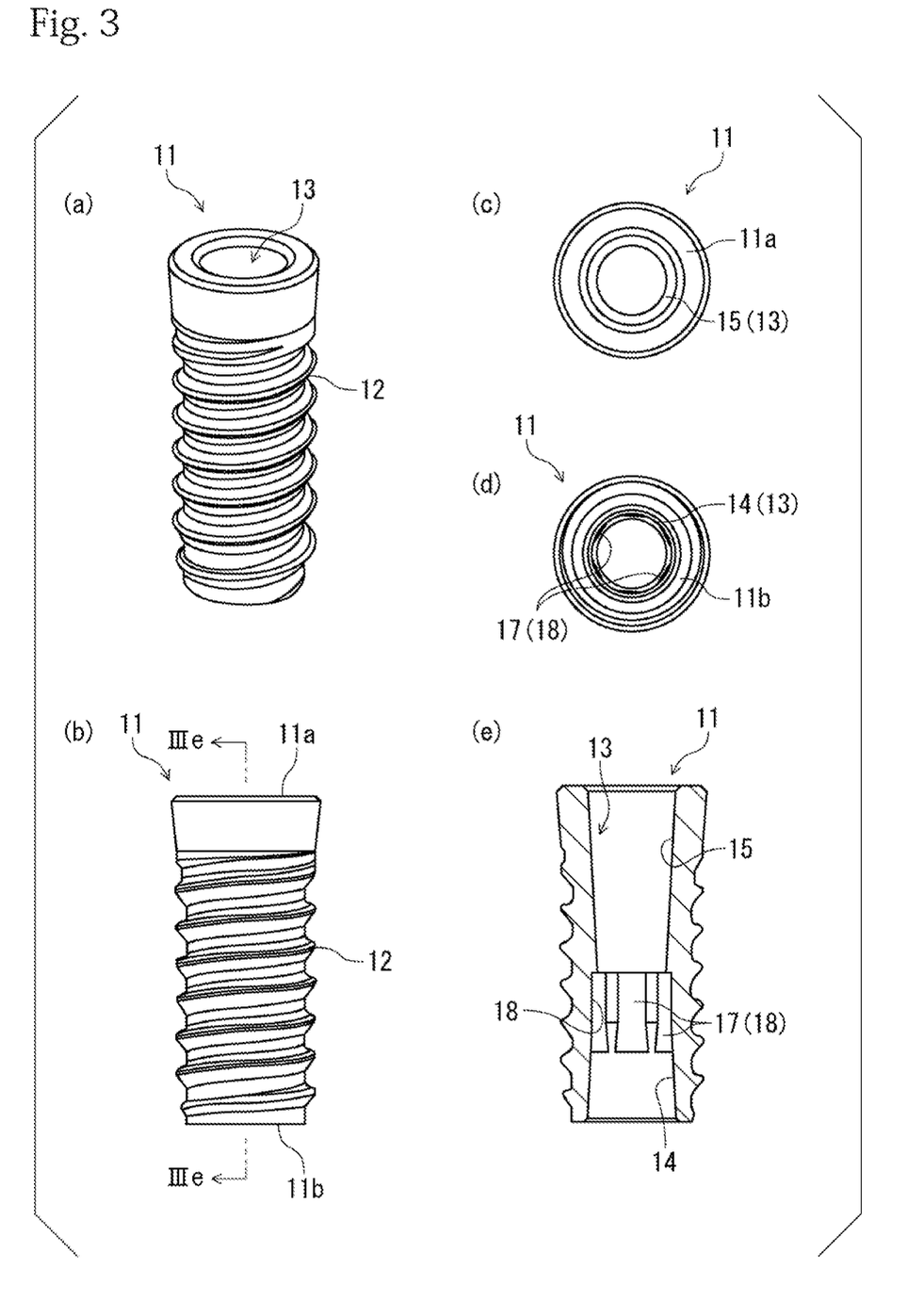
FIG. 3 illustrates a fixture body 11, including (a) perspective view, (b) front view, (c) top view, (d) bottom view, and (e) IIIe-IIIe sectional view.

FIG. 3 illustrates a fixture body 11, including (a) perspective view, (b) front view, (c) top view, (d) bottom view, and (e) IIIe-IIIe sectional view.

Figure 4:
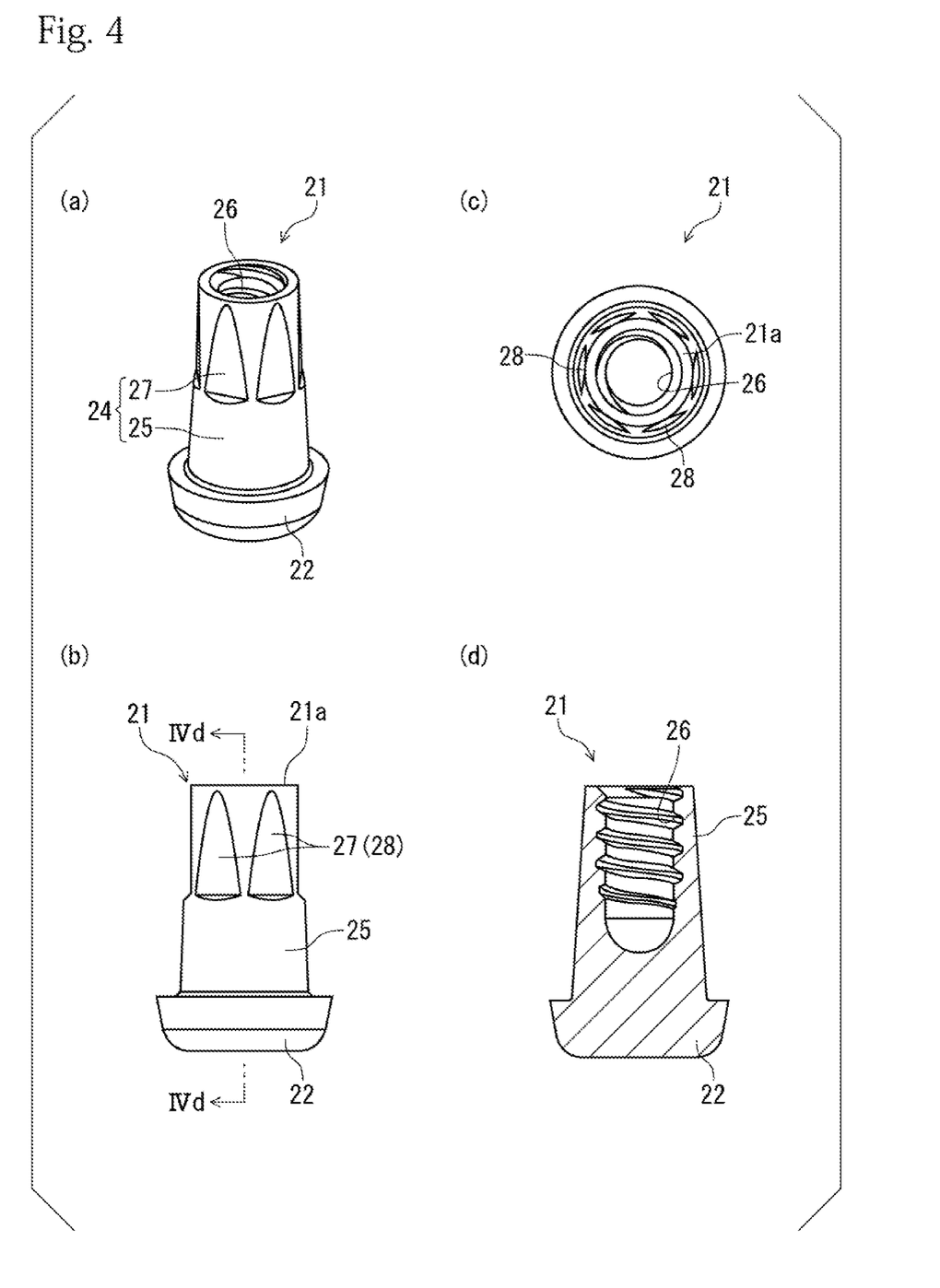
FIG. 4 illustrates a cap body 21, including (a) perspective view, (b) front view, (c) top view, and (d) IVd-IVd sectional view.

FIG. 4 illustrates views a cap body 21, including (a) perspective view, (b) front view, (c) top view, and (d) IVd-IVd sectional view.

The fixture 10 is a shaft-shaped member having a male screw 12 formed on its outer peripheral face, and has a non-penetrating central hole 13 excavated in the +Z direction. The fixture 10 has a maximum outer diameter of about 4.0 mm and an entire length of about 10.0 mm.

The fixture 10 comprises the fixture body 11 and the cap body 21.

The fixture body 11 is a cylindrical member and is formed of a ceramic material such as zirconia. The fixture body 11 has a maximum outer diameter of about 4.0 mm and a entire length of about 9.0 mm.

On an outer peripheral face of the fixture body 11, the male screw 12 is formed.

The central hole 13 is opened on a top end face 11a and a root end face 11b of the fixture body 11. The central hole 13 is a through hole penetrating the fixture body 11 along the Z direction. The central hole 13 has a minimum inner diameter of about 2.1 mm.

In the central hole 13, an inner diameter is small on the midportion and gradually enlarged (increases in diameter) toward the root end side and the top end side. In the central hole 13, a first tapered hole section 14 and a second tapered hole section 15 are continuously formed from the root end side toward the top end side.

In the first tapered hole section 14, the inner diameter is gradually narrowed (decreases in diameter) from the root end face 11b toward the −Z direction.

The first tapered hole section 14 has a taper angle of about 6°. The taper angle is preferably 0.1° to 10°. The length (depth) of the first tapered hole section 14 is about 4.0 mm. The length of the first tapered hole section 14 is preferably 20% (about 1.8 mm) or more to 50% (about 4.5 mm) or less of the entire length of the fixture body 11.

In the second tapered hole section 15, the inner diameter is gradually narrowed (decreases in diameter) from the top end face 11a toward the +Z direction.

The second tapered hole section 15 has a taper angle of about 6°. The taper angle is preferably 0.1° to 10°. The length (depth) of the second tapered hole section 15 is about 5.0 mm. The length of the second tapered hole section 15 is preferably 40% (about 3.6 mm) or more to 70% (about 6.3 mm) or less of the entire length of the fixture body 11.

The reason why the second tapered hole section 15 is made longer than the first tapered hole section 14 is that a large load (occlusal pressure) is applied to the second tapered hole section 15.

A hexagonal hole section (locked section) 17 is formed on the top end side of the first tapered hole section 14. The hexagonal hole section 17 comprises six locking claws 18 that radially project inward (in a direction toward the central axis C) from the inner peripheral face of the first tapered hole section 14. The hexagonal hole section consists of these six locking claws 18.

The cap body 21 is locked on the hexagonal hole section 17 (locking claws 18).

The cap body 21 is an umbrella-shaped member to be mounted on the root end face 11b of the fixture body 11, and is made of a ceramic material such as zirconia. The cap body 21 has an entire length of about 4.9 mm.

The cap body 21 has an umbrella section 22 and a first shaft section 24.

The umbrella section 22 is a frustoconical portion. The umbrella section 22 is in close contact with the root end face 11b and is exposed on the root end side of the fixture body 11.

The umbrella section 22 has a maximum outer diameter of about 3.2 mm and an entire length of about 1.0 mm.

The first shaft section 24 is a cylindrical portion and extends from the umbrella section 22 in the −Z direction. The first shaft section 24 consists of a first tapered shaft section 25 and a hexagonal shaft section 27.

The first tapered shaft section 25 is a portion extending over the entire length of the first shaft section 24, and the outer diameter thereof is gradually narrowed (decreases in diameter) toward the −Z direction.

The first tapered shaft section 25 is inserted into the central hole 13 of the fixture body 11 to close the opening on the root end side (first tapered hole section 14) of the central hole 13.

The first tapered shaft section 25 has a maximum outer diameter of about 2.4 mm. The first tapered shaft section 25 has a taper angle of about 6°. The taper angle is preferably 0.1° to 10°. The first tapered shaft section 25 has a length of about 3.9 mm. The length of the first tapered shaft section 25 is preferably 20% (about 1.8 mm) or more to 50% (about 4.5 mm) or less of the entire length of the fixture body 11.

The first tapered shaft section 25 has the same length and angle as those of the first tapered hole section 14, and is in close contact (taper-fitted) with the first tapered hole section 14.

The hexagonal shaft section (locking section) 27 is formed on the top end side of the first tapered shaft section 25. The hexagonal shaft section 27 consists of six locking grooves 28 recessed radially inward (in a direction toward the central axis C) from the outer peripheral face of the first tapered shaft section 25. These six locking grooves 28 form the hexagonal shaft section.

The hexagonal hole section 17 is fitted into the hexagonal shaft section 27. By bring the locking claws 18 into contact with the locking grooves 28, the hexagonal hole section 17 and the hexagonal shaft section 27 constitute a rotation stopper mechanism for preventing the circumferential rotation of the cap body 21 with respect to the fixture body 11.

A female screw 26 is provided on a top end face 21a of the cap body 21 (first tapered shaft section 25). The female screw 26 is excavated in the +Z direction from the top end face 21a. The female screw 26 has a size of e.g., M 1.4 and P 0.5.

The fixture 10 is assembled by inserting the first tapered shaft section 25 of the cap body 21 into the first tapered hole section 14 of the fixture body 11 and fitting the hexagonal shaft section 27 into the hexagonal hole section 17.

Since the first tapered hole section 14 and the first tapered shaft section 25 are in close contact (taper-fitted) with each other, the fixture body 11 and the cap body 21 are firmly connected to each other. In addition, since the locking claws 18 come into contact with the locking grooves 28, the cap body 21 does not circumferentially rotate with respect to the fixture body 11.

The first tapered hole section 14 is almost completely closed by the first tapered shaft section 25. Thereby, the top end face 21a of the cap body 21 becomes the bottom face of the central hole 13, and thus the central hole 13 has only the second tapered hole section 15. Consequently, the central hole 13 becomes a non-penetrating hole.

Abutment 30

Figure 5:
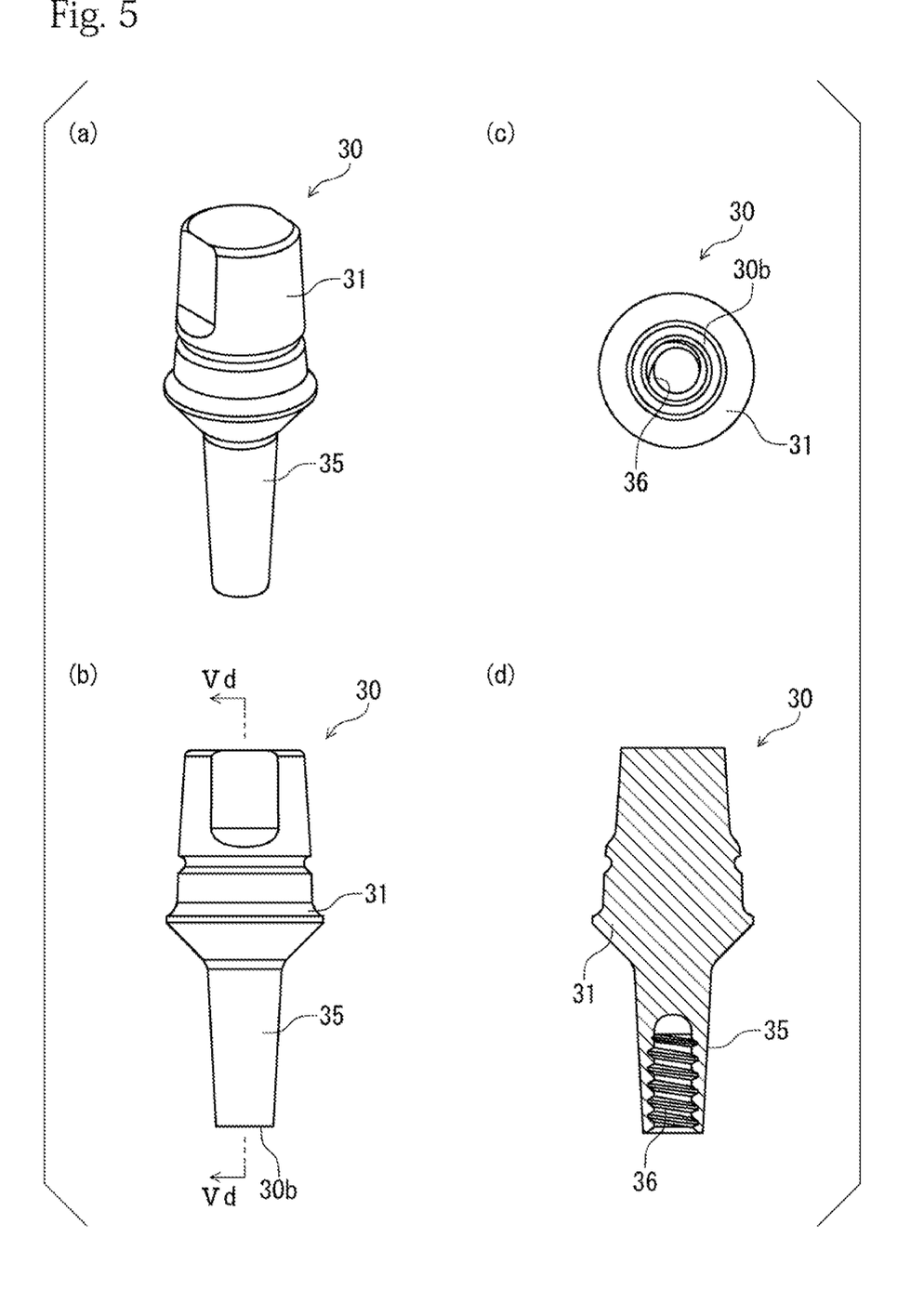
FIG. 5 illustrates an abutment 30, including (a) perspective view, (b) front view, (c) bottom view, and (d) Vd-Vd sectional view.

FIG. 5 illustrates an abutment 30, including (a) perspective view, (b) front view, (c) bottom view, and (d) Vd-Vd sectional view.

The abutment 30 is a shaft-shaped member and is formed of a ceramic material such as zirconia. The root end side of the abutment 30 is fitted into the central hole 13 of the fixture 10, and its top end side is exposed at the top end side of the fixture 10, and the implant crown 6 is mounted on the top end side.

The abutment 30 has a body section 31 and a second tapered shaft section 35.

The body section 31 is a substantially frustoconical portion and is exposed from the fixture 10. The implant crown 6 is fixed on the body section 31 using an adhesive, cement or the like.

The second tapered shaft section (second shaft section) 35 is a cylindrical portion and extends from the body section 31 in the +Z direction. The outer diameter of the second tapered shaft section 35 is gradually narrowed (decreases in diameter) toward the Z direction.

The second tapered shaft section 35 is inserted into the central hole 13 of the fixture body 11 to close the opening on the top end (second tapered hole section 15).

The second tapered shaft section 35 has a maximum outer diameter of about 2.4 mm. The second tapered shaft section 35 has a taper angle of about 6°. The taper angle is preferably 0.1° to 10°. The second tapered shaft section 35 has a length of about 5.0 mm. The length of the second tapered shaft section 35 is preferably 40% (about 3.6 mm) or more to 70% (about 6.3 mm) or less of the entire length of the fixture body 11.

The second tapered shaft section 35 has the same length and angle as those of the second tapered hole section 15, and is in close contact (taper-fitted) with the second tapered hole section 15.

A female screw 36 is provided on the root end face 30b of the abutment 30 (second tapered shaft section 35). The female screw 36 is excavated in the −Z direction from the root end face 30b. The female screw 36 has a size of e.g., M 1.4 and P 0.5.

The root end face 30b is disposed so as to be close to the bottom face (top end face 21a) of the central hole 13.

[Joint Screw 40]

Figure 6:
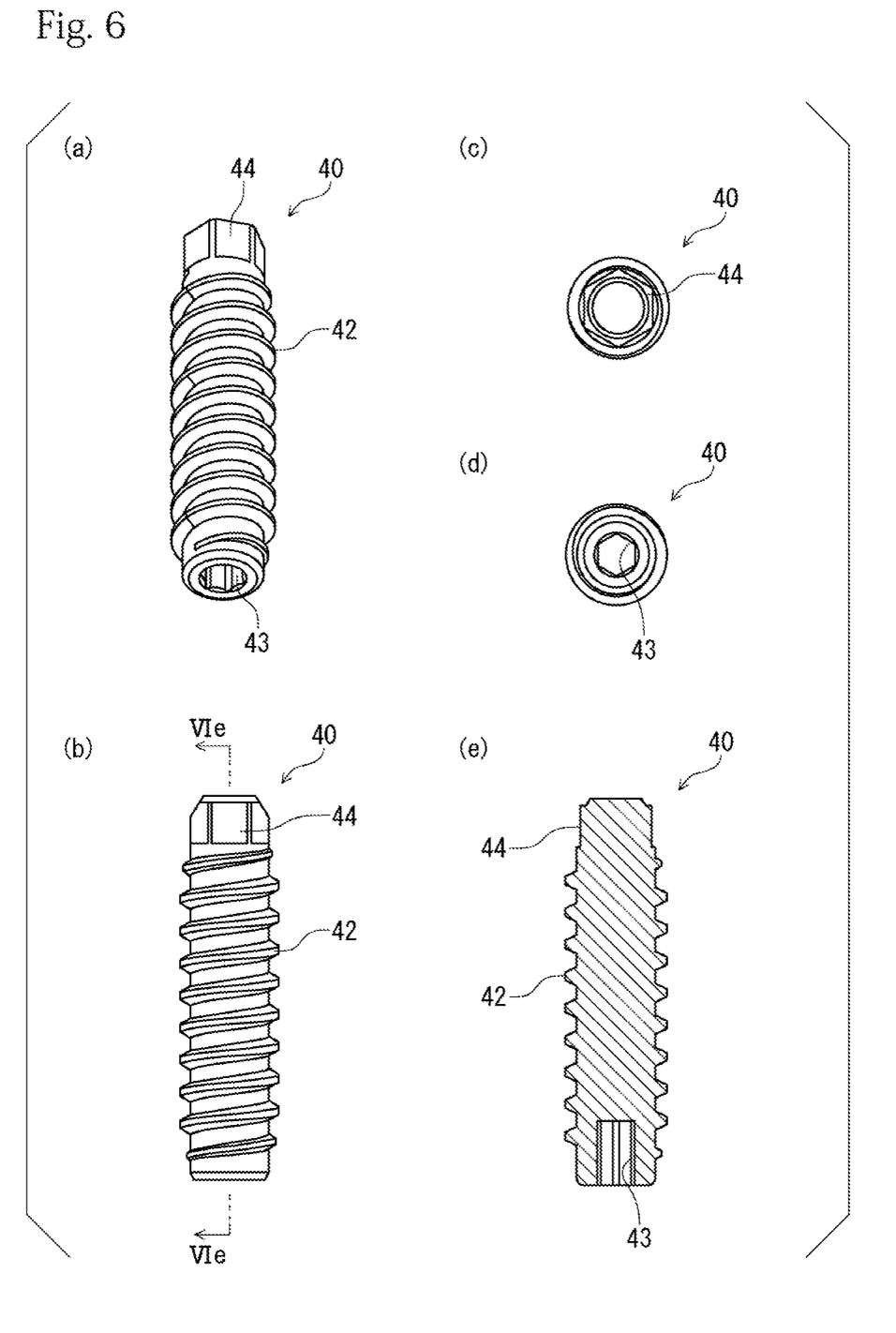
FIG. 6 illustrates a joint screw 40, including (a) perspective view, (b) front view, (c) top view, (d) bottom view, and (e) VIe-VIe sectional view.

FIG. 6 illustrates a joint screw 40, including (a) perspective view, (b) front view, (c) top view, (d) bottom view, and (e) VIe-VIe sectional view.

The joint screw (elastic member) 40 is a substantially cylindrical member disposed between the fixture 10 and the abutment 30. The joint screw 40 is a so-called screw shaft, on which a male screw 42 is formed over substantially the entire length.

The joint screw 40 is connected to the fixture 10 and the abutment 30. The joint screw 40 is screwed into the female screw 26 of the cap body 21 and the female screw 36 of the abutment 30 respectively. The cap body 21 and the abutment 30 are connected to each other through the joint screw 40.

The joint screw 40 is formed of a material having a higher elastic modulus than the fixture body 11 or the like. The joint screw 40 is made of an engineering plastic. The joint screw 40 is made of e.g., a thermoplastic resin. In particular, polyetheretherketone (PEEK) is suitable for the joint screw 40. Polyetheretherketone has high fatigue resistance, abrasion resistance, chemical resistance, radiation resistance, processability and dimensional stability.

The joint screw 40 is elastically deformed (stretched) by screwing it into the female screw 26 and the female screw 36 respectively. The joint screw 40 constantly generates a restoring force (axial force) of elastic deformation while screwed into the female screw 26 and the female screw 36 respectively.

The joint screw 40 draws the cap body 21 and the abutment 30 toward each other by this axial force. The joint screw 40 draws the cap body 21 and the abutment 30 toward the fixture body 11. Thereby, the first tapered shaft section 25 is pressed against the first tapered hole section 14, and the second tapered shaft section 35 is pressed against the second tapered hole section 15.

The coupling screw 40 generates an axial force while screwed into the female screw 26 and the female screw 36 respectively. Thereby, the male screw 42 is constantly in close contact with the female screw 26 and the female screw 36, and thus looseness of the screw hardly occurs.

The joint screw 40 has a hexagonal hole 43 formed at the top end and a hexagonal head 44 formed at the root end.

The hexagonal hole 43 is used for attaching (assembling) the joint screw 40 to the abutment 30. When the joint screw 40 is attached to the female screw 36, a hexagonal wrench (not shown in the figure) is inserted into the hexagonal hole 43 to impart a turning force to the joint screw 40.

The hexagonal head 44 is used when the joint screw 40 is detached (disassembled) from the fixture 10. When the joint screw 40 is detached from the female screw 26, the hexagonal head 44 is inserted into a hexagonal hole of a wrench (not shown in the figure) to impart a turning force to the joint screw 40.

[Method for Manufacturing the Dental Implant 1]

Each member of the dental implant 1 is formed (molded) of a biocompatible ceramic mainly composed of zirconia (zirconium oxide).

The manufacturing process for the fixture 10 (fixture body 11, cap body 21) includes a molding step and a sintering step, as well as various processing steps, a cleaning step, an assembly step, a γ-radiation sterilization step and a heating step.

Since the manufacturing process for the abutment 30 is the same as the fixture 10, explanation on it is omitted.

In the molding step, a pellet containing zirconia powder is injection-molded to obtain a zirconia compact (ceramic compact). That is, compacts of the fixture body 11 and the cap body 21 are obtained.

Next, in the sintering step, the zirconia compact is subjected to a pre-sintering treatment and a main sintering treatment. For example, sintering is carried out at 1500° C. or higher. Thereby, a zirconia sintered compact (ceramic sintered compact) is obtained. That is, sintered compacts of the fixture body 11 and the cap body 21 are obtained.

Subsequently, the various processing steps and the cleaning step are carried out.

In the various processing steps, the sintered compacts of the fixture body 11 and the cap body 21 are subjected to roughening treatment and the like. The roughening treatment is exemplified by a laser nonthermal processing.

Next, in the assembly step, the cap body 21 is mounted on the root end side of the fixture body 11. The first tapered shaft section 25 is inserted into the first tapered hole section 14 of the central hole 13, and the hexagonal shaft section 27 is fitted into the hexagonal hole section 17.

Next, a mount member (not shown in the figure) is inserted into the second tapered hole section 15 of the central hole 13 and screwed into the female screw 26 of the cap body 21.

Figure 7:
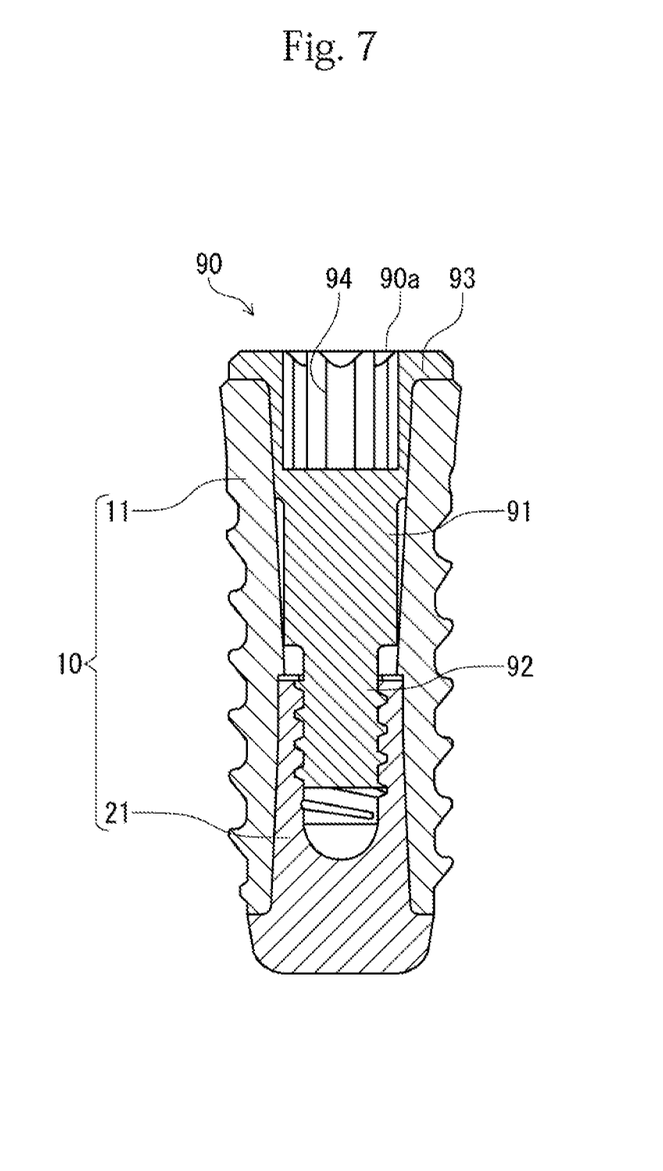
FIG. 7 illustrates a longitudinal sectional view of a fixture 10 connected to a cover member 90.

Instead of the abutment 30, the mount member closes the second tapered hole section 15 (see FIG. 7). The mount member is a member having a shaft section, a male screw and a grip, and is made of e.g., a thermoplastic resin. The shaft section has the substantially same shape as the second tapered shaft section 35. The male screw has the substantially same shape as the joint screw 40, and projects from the shaft section toward the root end side. The grip projects from the shaft section toward the top end side.

An operator can avoid foreign matters from adhering to the fixture 10 by grasping the grip using a dedicated jig.

A state that the first tapered hole section 14 and the first tapered shaft section 25 are in close contact with each other can be maintained by connecting the mount member to the fixture 10.

Finally, the γ-radiation sterilization step and the heating step are carried out.

Upon the γ-radiation sterilization step, the fixture body 11 and the like becomes dark brown. Thus, in the heating step, the fixture body 11 and the like are re-heated at 100 to 300° C. to restore (whiten) the color of the fixture body 11 and the like.

As described above, the fixture 10 is manufactured.

Note that, in the assembly step of the abutment 30, the joint screw 40 is screwed into the female screw 36.

[Two-Stage Method of Dental Implant Treatment]

FIG. 7 illustrates a longitudinal sectional view showing the fixture 10 connected to a cover member 90.

Installation of the dental implant 1 to the patient is performed in accordance with the following procedure.

(First Operation)

First, the fixture 10 is embedded in an alveolar bone H of a patient. The mount member is grasped to insert the fixture 10 into a hole formed in the alveolar bone H. The male screw 12 is screwed into the hole formed in the alveolar bone H to fix the fixture 10 to alveolar bone H.

Next, the mount member is removed and the cover member 90 is mounted on the fixture 10. The cover member 90 is inserted into the central hole 13 and screwed into the cap body 21.

Instead of the abutment 30, the cover member 90 closes the second tapered hole section 15 during bone bonding between the fixture 10 and the alveolar bone H. The cover member 90 is a member having a shaft section 91, a male screw 92 and a flange 93, and is made of e.g., a thermoplastic resin. The shaft section 91 has the substantially same shape as the second tapered shaft section 35. The male screw 92 has the substantially same shape as the joint screw 40 and projects from the shaft section 91 toward the root end side. The flange 93 is provided on the top end of the shaft section 91 and is in close contact with the top end face 11a of the fixture body 11. A hexagonal hole 94 is provided on a top end face 90a of the cover member 90.

An operator inserts a hexagonal wrench (not shown in the figure) into the hexagonal hole 94 to impart a turning force to the cover member 90.

A state that the first tapered hole section 14 and the first tapered shaft section 25 are in close contact with each other can be maintained by connecting the cover member 90 to the fixture 10.

Finally, the gum S is sutured. Subsequently, the alveolar bone H and the fixture 10 are brought into close contact with each other over e.g., about 3 to 6 months.

(Second Operation)

First, the gum S is incised, and the cover member 90 is removed from the fixture 10 which has been embedded in the alveolar bone H of the patient.

Next, the abutment 30 is connected to the fixture 10. The second tapered shaft section 35 of the abutment 30 is inserted into the central hole 13 (the second tapered hole section 15) of the fixture 10. Furthermore, the joint screw 40 connected to the root end of the abutment 30 is screwed into the female screw 26 of the cap body 21. Thereby, the second tapered hole section 15 and the second tapered shaft section 35 are brought into close contact with each other.

The root end face 30b of the abutment 30 is close to the bottom face (top end face 21a) of the central hole 13 with a slight gap therebetween. Consequently, the dental implant 1 becomes an integrated body (assembly) with little gap.

Finally, the gum S is sutured. Then, the implant crown 6 is mounted on the body section 31 of the abutment 30. An adhesive, cement or the like is disposed between the body section 31 and the implant crown 6. Thereby, the abutment 30 and the implant crown 6 are firmly connected to each other.

Subsequently, the gum S is conglutinated to the abutment 30 for e.g., about 2 weeks.

[Action of Dental Implant 1]

The fixture 10 comprises a fixture body 11 through which the central hole 13 penetrates over the entire length, and a cap body 21 which closes the opening on the root end side of the central hole 13. Since the central hole 13 penetrates through the fixture body 11, it can be easily formed and hardly causes defects. Since the opening (first tapered hole section 14) on the root end side of the central hole 13 is closed by the cap body 21, no trouble occurs during the implantation of the fixture into the patient.

Thus, the fixture 10 can be easily miniaturized, and it can be ensured to reduce defective products having defects such as cracks. Since the fixture 10 is constructed by integrating (assembling) the fixture body 11 and the cap body 21, the mechanical strength is high.

The cap body 21 has a first shaft section 24 fitted into the central hole 13. Thereby, it can be ensured to close the opening on the root end side (first tapered hole section 14) of the central hole 13.

The central hole 13 has the first tapered hole section 14 which decreases in diameter from the root end side toward the top end side, and the first shaft section 24 has the first tapered shaft section 25 which decreases in diameter from the root end side toward the top end side. Thereby, the first tapered hole section 14 and the first tapered shaft section 25 are in close contact with (taper-fitted) each other. Accordingly, the fixture body 11 and the cap body 21 are firmly connected to each other.

The first tapered hole section 14 and the first tapered shaft section 25 are formed so as to have a taper angle of 0.1° to 10°. The lengths of the first tapered shaft section 25 and the first tapered hole section 14 are 20% or more to 50% or less of the entire length of the fixture body 11. Thereby, it is ensured that the first tapered hole section 14 and the first tapered shaft section 25 are in close contact with each other, so that the fixture body 11 and the cap body 21 are firmly connected to each other.

The fixture body 11 comprises a rotation stopper mechanism. The fixture body 11 comprises the hexagonal hole section 17 formed on the inner surface of the central hole 13, and the cap body 21 comprises a hexagonal shaft section 27 formed on the first shaft section 24. Thereby, the hexagonal shaft section 27 is fitted into the hexagonal hole section 17, and the locking claws 18 and the locking grooves 28 come into contact with each other, so that the circumferential rotation of the cap body 21 with respect to the fixture body 11 is suppressed.

The conventional ceramic fixture is a single member, of which the mechanical strength depends on the flow direction of the raw material (ceramic powder) in the molding step.

Since ceramics such as zirconia are polycrystalline, each crystal is oriented in the flow direction by powder injection molding. Thereby, the compacts such as the fixture have anisotropy of the mechanical strength. Specifically, the mechanical strength in the flow direction of the powder in the mold is increased, and the mechanical strength in the direction perpendicular thereto is decreased.

Thus, the conventional ceramic fixture has a low mechanical strength in a certain direction due to the anisotropy of the mechanical strength.

In contrast, the fixture 10 is an integrated body (assembly) constructed by combining the fixture body 11 with the cap body 21.

As in the conventional way, the fixture body 11 and the cap body 21 are respectively formed by injection molding of a ceramic powder, and thus they have anisotropy of mechanical strength.

Note that, since the fixture body 11 and the cap body 21 are separately molded, they have different flow directions of the raw material in the molding step. That is, the fixture body 11 and the cap body 21 have different anisotropic directions of the mechanical strength.

Since the fixture 10 is constructed by integrating (assembling) the fixture body 11 and the cap body 21, the directionality of the mechanical strength is dispersed. In other words, the fixture 10 becomes nearly isotropic by cancellation between the anisotropy of the fixture body 11 and the cap body 21.

Consequently, the fixture 10 has a higher mechanical strength than the conventional fixture. In addition, unevenness of the mechanical strength is reduced when the fixture 10 is mass-produced. The mechanical strength of the fixture 10 can be equalized (stabilized).

The dental implant 1 comprises a fixture 10, and an abutment 30 having a second tapered shaft section 35 to be fitted into the central hole 13 (the second tapered hole section 15). Thereby, in the dental implant 1, the central hole 13 is almost completely filled with the first tapered shaft section 25 and the second tapered shaft section 35, so that the mechanical strength is improved.

The central hole 13 has the second tapered hole section 15 which decreases in diameter from the top end side toward the root end side, and the second tapered shaft section 35 decreases in diameter from the top end side toward the root end side. Thereby, the second tapered hole section 15 and the second tapered shaft section 35 are in close contact (taper-fitted) with each other. Accordingly, the fixture body 11 and the abutment 30 are firmly connected to each other.

The second tapered hole section 15 and the second tapered shaft section 35 are formed so as to have a taper angle of 0.1° to 10°. The length of the second tapered hole section 15 and the second tapered shaft section 35 are 40 to 70% of the entire length of the fixture body 11. Thereby, it is ensured that the second tapered hole section 15 and the second tapered shaft section 35 are in close contact with each other, so that the fixture body 11 and the abutment 30 are firmly connected to each other.

The root end face 30b of the abutment 30 is close to the bottom face (top end face 21a) of the central hole 13. Thereby, the dental implant 1 has little gap, and its mechanical strength is improved.

The abutment 30 is formed by injection molding of a ceramic powder. The abutment 30 is formed separately from the fixture body 11 and the cap body 21. Thereby, the flow direction of the raw material of the abutment 30 in the molding step is different from that of the fixture body 11 or the like. That is, the abutment 30 has the anisotropic direction of the mechanical strength different from those of the fixture body 11 and the cap body 21.

Since the dental implant 1 is constructed by integrating (assembling) the fixture body 11, the cap body 21 and the abutment 30, the directionality of the mechanical strength is dispersed. In other words, the dental implant 1 becomes nearly isotropic by cancellation among the anisotropy of the fixture body 11, the cap body 21, and the abutment 30.

Consequently, the dental implant 1 has a higher mechanical strength than the conventional dental implant. In addition, unevenness of the mechanical strength is reduced when the dental implant 1 is mass-produced. The mechanical strength of the dental implant 1 can be equalized (stabilized).

The dental implant 1 comprises the joint screw 40 which is disposed between the cap body 21 and the abutment 30 and connected to the cap body 21 and the abutment 30. The joint screw 40 has male screws 42 formed at both ends and is screwed into the female screws 26 and 36.

The joint screw 40 extends to be connected to the cap body 21 and the abutment 30. By the restoring force (axial force) of the joint screw 40, the first tapered shaft section 25 is pressed against the first tapered hole section 14, and the second tapered shaft section 35 is pressed against the second tapered hole section 15.

The cap body 21 and the abutment 30 are arranged to face each other along the central axis C, further pressed against and taper-fitted into the fixture body 11. Thereby, the fixture body 11, the cap body 21 and the abutment 30 are tightly connected.

The male screw 42 of the joint screw 40 is in close contact with the female screw 26 and the female screw 36. The joint screw 40 constantly generates a large frictional force between the female screws 26 and 36, and thus looseness of the screw hardly occurs.

Hence, a firmly-connected state that the fixture body 11, the cap body 21 and the abutment 30 are in close contact with each other is maintained over a long period.

The joint screw 40 is made of a thermoplastic resin, particularly a polyetheretherketone resin. Since the joint screw 40 is made of a material different from those of the fixture 10 and the abutment 30, it has a different sound (vibration) transmission property from those of the fixture 10 and the abutment 30. For this reason, unpleasant occlusal sounds can be reduced.

Consequently, the dental implant 1 can reduce vibrations due to occlusion to suppress (reduce) generation of unpleasant occlusal sounds.

As described above, the fixture 10 which facilitates formation of the central hole 13 and reduces defects such as cracks can be achieved. Particularly in the fixture 10 made of a ceramic, occurrence of defects in the central hole 13 can be prevented. Thus, it can be ensured to miniaturize the fixture 10 and the dental implant 1.

It can be ensured that the fixture 10 and the dental implant 1 is highly strengthened because they are made as an integrated body (assembly) constructed by combining a plurality of members. In particular, the fixture 10 and the dental implant 1 made of the ceramic are highly strengthened by lowering the anisotropy of the mechanical strength of each member (dispersing the directionality).

Since the dental implant 1 is constructed by connecting the fixture 10 with the abutment 30 through the joint screw 40, the firmly-connected state can be maintained for a long period.

In the dental implant 1, the joint screw 40 can reduce vibrations due to occlusion to suppress (reduce) generation of unpleasant occlusal sounds.

The present invention is not limited to the above-described embodiments, but includes the embodiments with various modifications without departing from the purpose of the present invention. That is, the specific shapes, configurations and the like cited in the embodiments are merely examples, and can be appropriately changed.

For example, in the above-described embodiments, the dental implant has been explained as an example, but the implant may be a hip prosthesis. The fixture and the implant according to the present invention can be used for a fixture and an implant of a hip prosthesis.

The members such as the fixture 10 (fixture body 11, cap body 21), the abutment 30 and the implant crown 6 may be formed of a biocompatible ceramic material such as alumina (aluminum oxide), yttrium oxide, hafnium oxide, silicone oxide, magnesium oxide and cerium oxide.

These members may be combinations of zirconia with a metal and an alloy. The metal and the alloy refer to copper, titanium, a titanium alloy or the like.

These members may be combinations of zirconia with carbon, resin, glass or the like.

These members may be formed of metal materials such as titanium and a titanium alloy.

The second tapered hole section 15 and the first tapered hole section 14 are not limited to those of the tapered shape, and may be shaped into a straight (cylindrical) hole.

The first tapered shaft section 25 and the second tapered shaft section 35 are not limited to those of the tapered shape, and may be shaped into a straight (cylindrical) shaft.

The dental implant 1 is not limited to implants for front teeth (upper front teeth), and may be an implant for back teeth.

The implant (dental implant, hip prosthesis implant) may be applied to not only humans but also pets such as dogs and cats, and livestock such as cattle and horses.

An adhesive, cement or the like may be disposed between the first tapered hole section 14 and the first tapered shaft section 25. Thereby, the fixture body 11 and the cap body 21 are more firmly connected to each other.

An adhesive, cement or the like may be disposed (applied) between the second tapered hole section 15 and the second tapered shaft section 35. Thereby, the fixture body 11 and the abutment 30 are more firmly connected to each other.

The first tapered hole section 14 and the first tapered shaft section 25 do not necessarily have the same length, and the second tapered hole section 15 and the second tapered shaft section 35 do not necessarily have the same length.

The first tapered hole section 14 and the second tapered hole section 15 are not necessarily formed continuously. A non-tapered hole section may be provided between the first tapered hole section 14 and the second tapered hole section 15.

The rotation stopper mechanism is not necessarily the hexagonal hole section 17 and the hexagonal shaft section 27. It may have a shape other than hexagon. The rotation stopper mechanism may be provided on the root end of the fixture body 11 and the umbrella section 22 of the cap body 21.

The hexagonal hole section 17 is not necessarily formed (integrally formed) on a part of the first tapered hole section 14. The hexagonal shaft section 27 is not necessarily formed on a part of the first tapered shaft section 25. The hexagonal hole section 17 and the first tapered shaft section 25 may be separately formed, and the hexagonal shaft section 27 and the first tapered hole section 14 may be separately formed.

The joint screw 40 does not necessarily have the male screw 42 formed over the entire length thereof. It is only necessary to form the male screws 42 on the both ends.

The joint screw 40 is not necessarily the screw shaft (male screw), and may be a nut (female screw). That is, male screws may be respectively formed on the top end of the cap body 21 and the root end of the abutment, and the male screws may be screwed into a nut-shaped joint screw.

1 dental implant (implant)
6 implant crown
10 fixture
11 fixture body
11a top end face
11b root end face
12 male screw
13 central hole
14 first tapered hole section
15 second tapered hole section
17 hexagonal hole section (locked section)
18 locking claw
21 cap body
21a top end face
22 umbrella section
24 first shaft section
25 first tapered shaft section
26 female screw
27 hexagonal shaft section (locking section)
28 locking groove
30 abutment
30b root end face
31 body section
35 second tapered shaft section (second shaft section)
36 female screw
40 joint screw (elastic member)
42 male screw
43 hexagonal hole
44 hexagonal head
C central axis
H alveolar bone (bone)
S gum

The invention claimed is:

1. An implant to be embedded in a bone, comprising:
a fixture body through which a central hole penetrates over the entire length of the fixture body, the central hole comprising a first tapered hole section which decreases in diameter from a root end side toward a top end side and a second tapered hole section which decreases in diameter from the top end side toward the root end side; and
a cap body arranged on an opening on the root end side of the central hole and having a first tapered shaft section to be fitted in the first tapered hole, and
an abutment arranged on an opening on the top end side of the central hole and having a second tapered shaft section to be fitted into the second tapered hole section;
wherein the fixture body, the cap body and the abutment are injection-molded articles of a ceramic powder,
wherein the fixture body, the cap body, and the abutment have different anisotropic directions of mechanical strength due to respective orientation of crystals,
wherein the cap body has a hole formed only on a top end side thereof, and
wherein the abutment has a hole formed only on a root end side thereof.

2. The implant according to claim 1, wherein the first tapered hole section and the first tapered shaft section are formed so as to have a taper angle of 0.1° to 10°.

3. The implant according to claim 1, wherein the first tapered hole section and the first tapered shaft section have a length of 20% or more to 50% or less of the entire length of the fixture body.

4. The implant according to claim 1,
wherein the fixture body comprises a locked section formed on an inner surface of the central hole;
wherein the cap body comprises a locking section formed on the first tapered shaft section; and
wherein the locked section comes into contact with the locking section to restrain rotation of the cap body with respect to the fixture body.

5. The implant according to claim 1, wherein the second tapered hole section and the second tapered shaft section have a taper angle of 0.1° to 10°.

6. The implant according to claim 1, wherein the second tapered hole section and the second tapered shaft section have a length of 40% or more to 70% or less of the entire length of the fixture body.

7. The implant according to claim 1, wherein the cap body and the abutment are close to each other in the central hole.

8. The implant according to claim 1, further comprising an elastic member which is disposed between the cap body and the abutment and connected to the cap body and the abutment, and which is formed of a material having a higher elastic modulus than the cap body, the abutment and the fixture body,
wherein the elastic member is elastically deformable when connected to the cap body and the abutment and constantly draws the cap body and the abutment toward the fixture body.

9. The implant according to claim 8, wherein
the elastic member has screw sections on both ends in a longitudinal direction; and
the hole of the cap body and the hole of the abutment body has a screw section into which the elastic member is screwed.

10. The implant according to claim 8, wherein the elastic member is made of a thermoplastic resin.

11. The implant according to claim 10, wherein the thermoplastic resin is a polyetheretherketone resin.

12. The implant according to claim 1, wherein the implant is a dental implant to be embedded in an alveolar bone.

13. A method of manufacturing an implant to be embedded in a bone, comprising:
separately injection molding a fixture body of a fixture, a cap body of the fixture, and an abutment, by injection-molding a ceramic powder so that the fixture body, the cap body and the abutment have different anisotropic directions of mechanical strength due to respective orientation of crystals,
wherein the fixture body comprises a central hole which penetrates over the entire length of the fixture body, the central hole comprising a first tapered hole section which decreases in diameter from a root end side toward a top end side and a second tapered hole section which decreases in diameter from the top end side toward the root end side;
wherein the cap body is configured to be arranged on an opening on the root end side of the central hole;
wherein the abutment comprises a shaft section configured to be fitted into the central hole, and
wherein the cap body has a hole formed only on a top end side thereof, and
wherein the abutment has a hole formed only on a root end side thereof.

14. The method according to claim 13,
wherein an elastic member is capable of being disposed between the cap body and the abutment and connected to the cap body and the abutment, and which is formed of a material having a higher elastic modulus than the cap body, the abutment, and the fixture body, and
wherein the elastic member is elastically deformable when connected to the cap body and the abutment and constantly draws the cap body and the abutment toward the fixture body.

* * * * *